US 8,187,189 B2

(12) United States Patent
Jung et al.

(10) Patent No.: US 8,187,189 B2
(45) Date of Patent: May 29, 2012

(54) IMAGING VIA BLOOD VESSELS (75) Inventors: Edward K. Y. Jung, Bellevue, WA (US);
Eric C. Leuthardt, St. Louis, MO (US);
Royce A. Levien, Lexington, MA (US);
Robert W. Lord, Seattle, WA (US);
Mark A. Malamud, Seattle, WA (US);
John D. Rinaldo, Jr., Bellevue, WA
(US); Clarence T. Tegreene, Bellevue,
WA (US); Lowell L. Wood, Jr.,
Livermore, CA (US)

(73) Assignee: The Invention Science Fund I, LLC,
Bellevue, WA (US)

( * ) Notice: Subject to any disclaimer, the term of this patent is extended or adjusted under 35 U.S.C. 154(b) by 1497 days.

(21) Appl. No.: 11/414,164

(22) Filed: Apr. 28, 2006

(65) Prior Publication Data

US 2007/0255097 A1 Nov. 1, 2007

(51) Int. Cl.
*A61B 6/00* (2006.01)
(52) U.S. Cl. ........................ 600/443; 600/454
(58) Field of Classification Search ............... 600/443, 600/454
See application file for complete search history.

(56) References Cited

U.S. PATENT DOCUMENTS

| 4,567,898 | A | * | 2/1986 | Plugge et al. ............... 600/443 |
| 4,817,622 | A | | 4/1989 | Pennypacker et al. |
| 4,887,605 | A | * | 12/1989 | Angelsen et al. ............ 600/439 |
| 5,810,757 | A | | 9/1998 | Sweezer, Jr. et al. |
| 5,833,596 | A | | 11/1998 | Bonnell et al. |
| 6,026,814 | A | | 2/2000 | LaFontaine et al. |
| 6,192,267 | B1 | | 2/2001 | Scherninski et al. |
| 6,610,007 | B2 | | 8/2003 | Belson et al. |
| 6,816,743 | B2 | | 11/2004 | Moreno et al. |
| 6,899,675 | B2 | | 5/2005 | Cline et al. |
| 7,837,617 | B2 | * | 11/2010 | Mori et al. ............... 600/118 |
| 2002/0177846 | A1 | | 11/2002 | Mulier et al. |
| 2003/0135101 | A1 | | 7/2003 | Webler |
| 2003/0220541 | A1 | | 11/2003 | Salisbury, Jr. et al. |
| 2004/0082850 | A1 | | 4/2004 | Bonner et al. |
| 2004/0092960 | A1 | | 5/2004 | Abrams et al. |
| 2004/0193010 | A1 | * | 9/2004 | Fujimori et al. ............ 600/118 |
| 2005/0014995 | A1 | | 1/2005 | Amundson et al. |
| 2005/0015123 | A1 | | 1/2005 | Paithankar |
| 2005/0043718 | A1 | | 2/2005 | Madhani et al. |
| 2005/0049624 | A1 | | 3/2005 | Francese et al. |
| 2005/0085725 | A1 | * | 4/2005 | Nagar et al. ............... 600/437 |
| 2005/0090711 | A1 | | 4/2005 | Fuchs et al. |
| 2005/0197574 | A1 | | 9/2005 | Eberle et al. |
| 2005/0197623 | A1 | | 9/2005 | Leeflang et al. |
| 2006/0020309 | A1 | | 1/2006 | Altshuler et al. |
| 2006/0030841 | A1 | | 2/2006 | Madhani et al. |
| 2006/0036164 | A1 | | 2/2006 | Wilson et al. |
| 2006/0052661 | A1 | | 3/2006 | Gannot et al. |
| 2006/0073100 | A1 | | 4/2006 | Fischman et al. |

OTHER PUBLICATIONS

PCT International Search Report; International Application No. PCT/US 07/10310; pp. 1-2; dated Mar. 5, 2008.
Bartz, Dirk; "Extraction and Visualization of Coronary Vascular Structures"; 2003 Curac; pp. 1-2; Univeritat Erlangen-Nurnberg.

(Continued)

*Primary Examiner* — Tse Chen
*Assistant Examiner* — Vani Gupta (57) ABSTRACT

A method and system are described for generating a signal indicative of an intravascular image received at least partly via a light transducer and invoking circuitry for passing the generated signal out of a subject's body.

24 Claims, 11 Drawing Sheets

OTHER PUBLICATIONS

Kypson, Alan P.; Chitwood, Jr., W. Randolph; "Robotic Applications in Cardiac Surgery"; International Journal of Advanced Robotic Systems; Bearing dates of 2004 and Jun. 2004; pp. 87-92; vol. 1, No. 2.

"LAP Mentor: Practice Surgery on a Virtual Patient"; pp. 1-4; located at: www.simbionix.com.

Mizuno, Kyoichi; Sakai, Shunta; Ohkuni, Shinichi; Jing, Zhang; Hayakawa, Hirokazu; "Reviews: The Development and Clinical Feasibility of Percutaneous Transluminal Coronary Angioscopy"; Journal of Nippon Medical School; Bearing a date of 1999; pp. 7-14; vol. 66, No. 1; The Medical Association of Nippon Medical School.

Vasile, M.J.; Nassar, R.; Xie, J.; Guo, H.; "Microfabrication Techniques Using Focused Ion Beams and Emergent Applications"; Micron; Bearing a date of 1999; pp. 235-244; vol. 30; Elsevier Science Ltd.; located at: www.elsevier.com/locate/micron.

* cited by examiner

IMAGING VIA BLOOD VESSELS

SUMMARY

An embodiment provides a method. In one implementation, the method includes but is not limited to generating a signal indicative of an intravascular image received at least partly via a light transducer and invoking circuitry for passing the generated signal out of a subject's body. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for generating a signal indicative of an intravascular image received at least partly via a light transducer and circuitry for passing the generated signal out of a subject's body. In addition to the foregoing, other system aspects are described in the claims, drawings, and text forming a part of the present disclosure.

In addition to the foregoing, various other embodiments are set forth and described in the text (e.g., claims and/or detailed description) and/or drawings of the present description.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1:
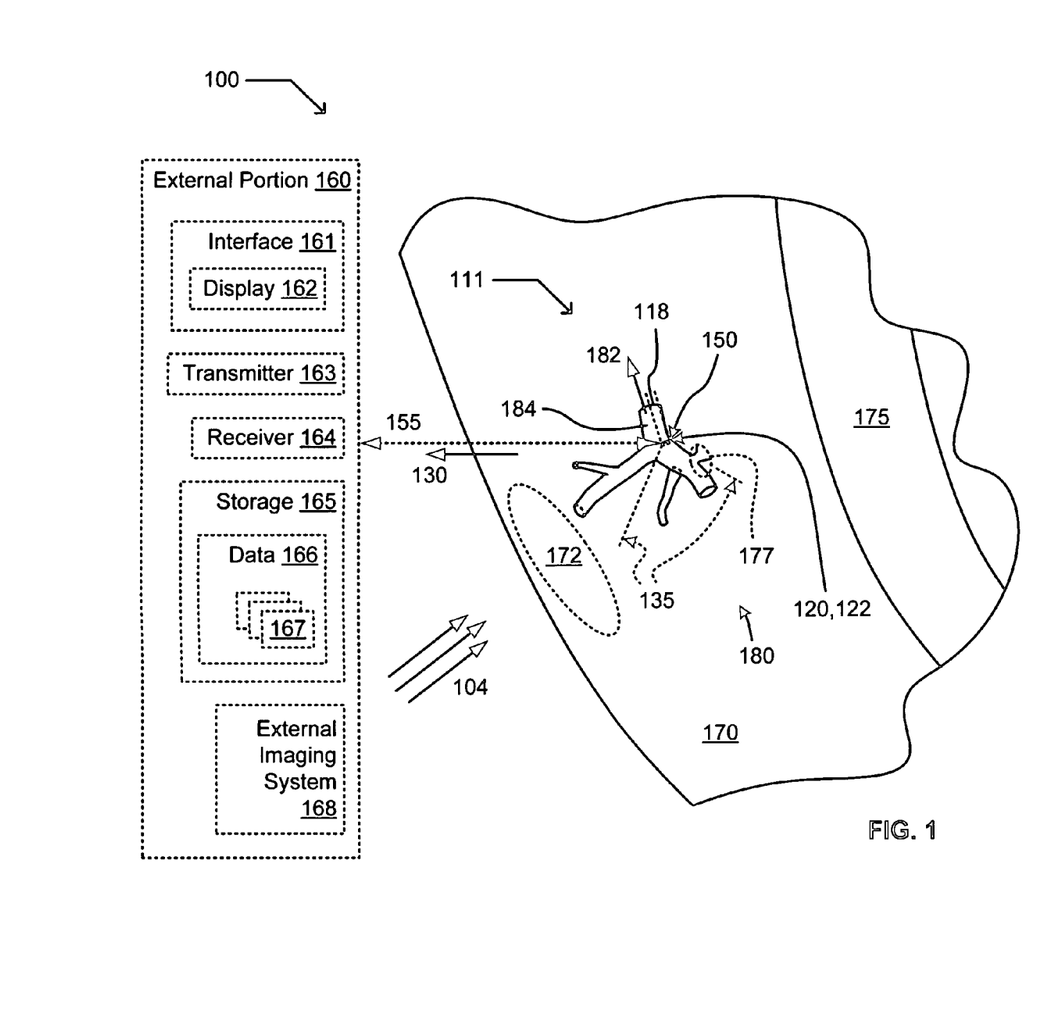
FIG. 1 depicts an exemplary environment in which one or more technologies may be implemented.

Referring now to FIG. 1, there is shown an exemplary environment in which one or more technologies may be implemented. As shown system 100 comprises vascular probe 111 having at least an intravascular portion 118 inside vascular system 180 of a subject's body 170. In some embodiments as described below, "subject" refers to a human being, living or otherwise, or a single mammal or other animal in a population. Portion 118 extends within an artery, capillary or other blood vessel 184 so as to occlude flow path only partially. Portion 118 comprises imaging/control circuitry 120 including at least light transducer 122 having a field of view 135 at least partly including target 177. At least a portion of imaging/control circuitry 120 invokes communication circuitry 150, which can respond by transmitting at least image-indicative signal(s) 130 along path 155 out of the subject's body 170. In some embodiments, "circuitry" comprises amplifiers, logic, or other active elements coupled by conduits.

System 100 can further include an external portion 160 comprising one or more of interface 161, transmitter 163, receiver 164, storage 165, or external imaging system 168. Interface 161 can include display 162. Storage 165 can contain data 166 comprising images 167. External imaging system 168 can emit energy 104 toward tissue 172, a portion of which energy penetrates body 170 into blood vessel 184 or a bone or other reference structure 175.

Figure 2:
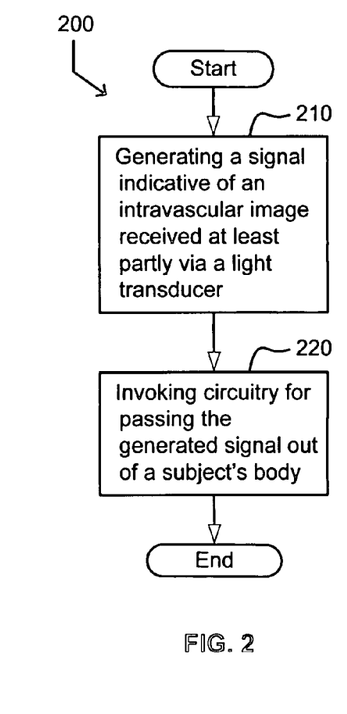
FIG. 2 depicts a high-level logic flow of an operational process.

Referring now to FIG. 2, there is shown a high-level logic flow 200 of an operational process. Operation 210 describes generating a signal indicative of an intravascular image received at least partly via a light transducer (e.g. imaging/control circuitry 120 providing an image of a lesion captured through light transducer 122). In some embodiments, the image can be intravascular by virtue of a primary target or sensor extending within a blood vessel, for example. In some embodiments, a probe performs operation 210 by capturing an image of an easily recognized structure intravascularly (e.g. vascular probe 111 capturing an image of a large bone, e.g.) as a navigational reference. Operation 220 describes invoking circuitry for passing the generated signal out of a subject's body (e.g. imaging control circuitry 120 invoking communication circuitry 150 to pass signal(s) 130 out of body 170). In some embodiments, this can comprise transmitting or otherwise transferring the signal from inside the body. Signal(s) 130 can pass through an antenna (not shown) or otherwise along path 155, for example.

Figure 3:
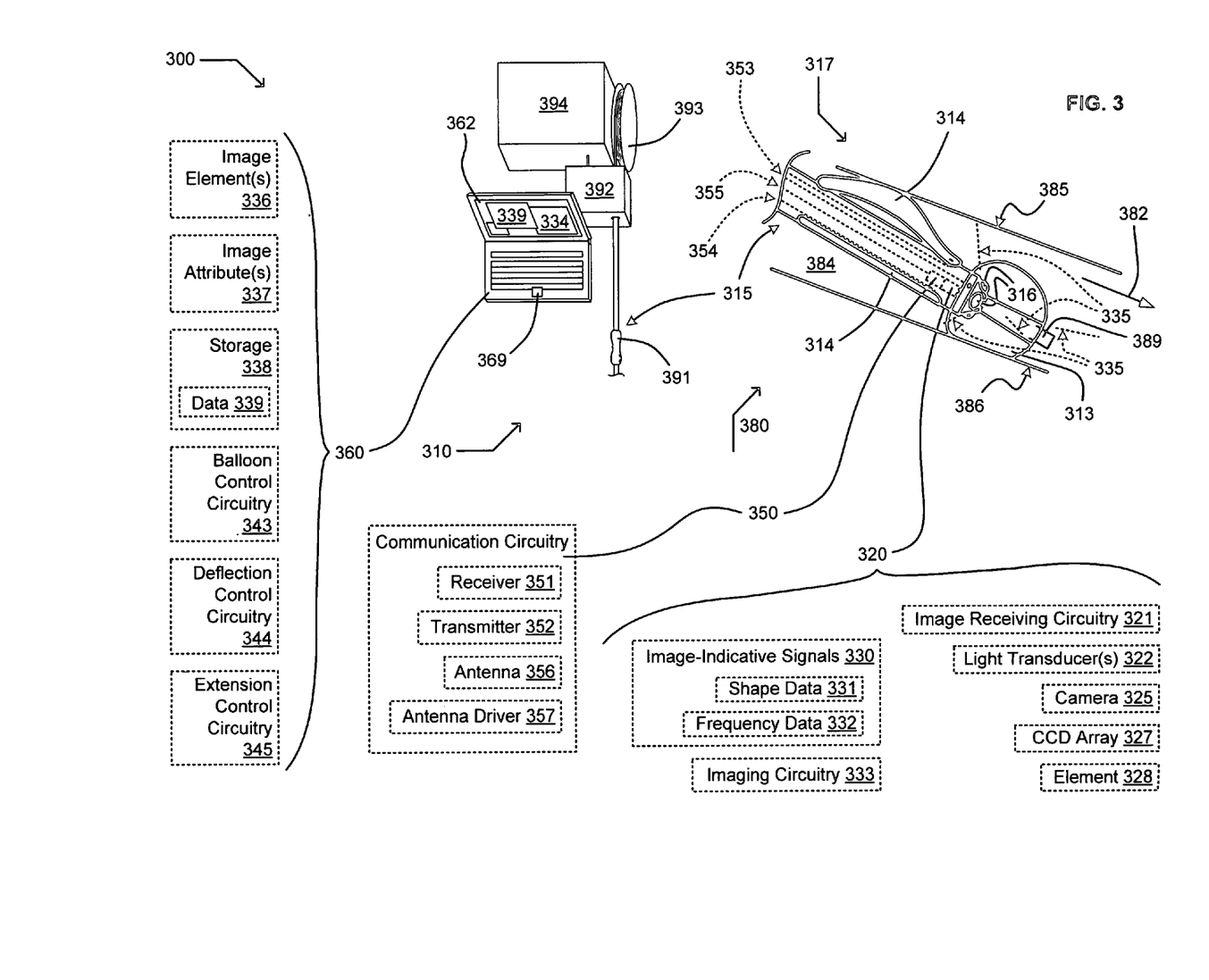
FIG. 3 depicts another exemplary environment in which one or more technologies may be implemented.

Referring now to FIG. 3, there is shown another exemplary environment in which one or more technologies may be implemented. As shown system 300 comprises laparoscopic system 310 including catheter 315 with at least a distal intravenous portion 317 inside vein 384 of vascular system 380. Portion 317 occludes flow path 382 only partially. Portion 317 comprises one or more of imaging/control circuitry 320 or communication circuitry 350. Imaging/control circuitry 320 can optionally comprise one or more of image receiving circuitry 321, light transducer(s) 322, camera 325, charge coupled device (CCD) array 327, element 328, image-indicative signals 330, or imaging circuitry 333. Image-indicative signals 330 can optionally comprise one or more of shape data 331 or frequency data 332.

Communication circuitry 350 can optionally comprise one or more of receiver 351, transmitter 352, antenna 356, or antenna driver 357 able to communicate with hub 392 via conduit 355. One or more elements of imaging/control circuitry 320 are configured to receive (reflected or other) optical energy from a respective field of view 335 for each of one or more lenses 316. The presence of blood in vein 384 limits imaging effectiveness, though, especially in the visible spectrum. To reduce an amount of blood immediately around lenses 316, balloon 313 can be inflated and deflated selectively by balloon control circuitry 343 through (air or other) fluid line 353. One or more other deflectors 314 can likewise be actuated and de-actuated selectively, for example, by deflection control circuitry 344 via electrical or fluid line 354. By actuating upper deflector 314 to bear against wall 385 as shown, for example, the one or more lenses 316 closest to wall 386 are moved closer, enabling a clearer view of wall 386 through balloon 313. In some embodiments, extension 389 can be steered, advanced, retracted or otherwise manipulated via extension control circuitry 345.

In some embodiments, hub 392 can comprise one or more of a fluid or other supply 394, a spool 393 (for use with extension 389, e.g.), a laparoscopic controller 391, and an external portion 360. External portion 360 can comprise one or more input device(s) 369, a screen 362 configured to display intravascular/video images 334 and other image data 339 such as that from an ultrasound or other external imaging system (not shown). External portion 360 can likewise include one or more of image element(s) 336, image attribute(s) 337, or storage 338 having the other image data 339.

Figure 4:
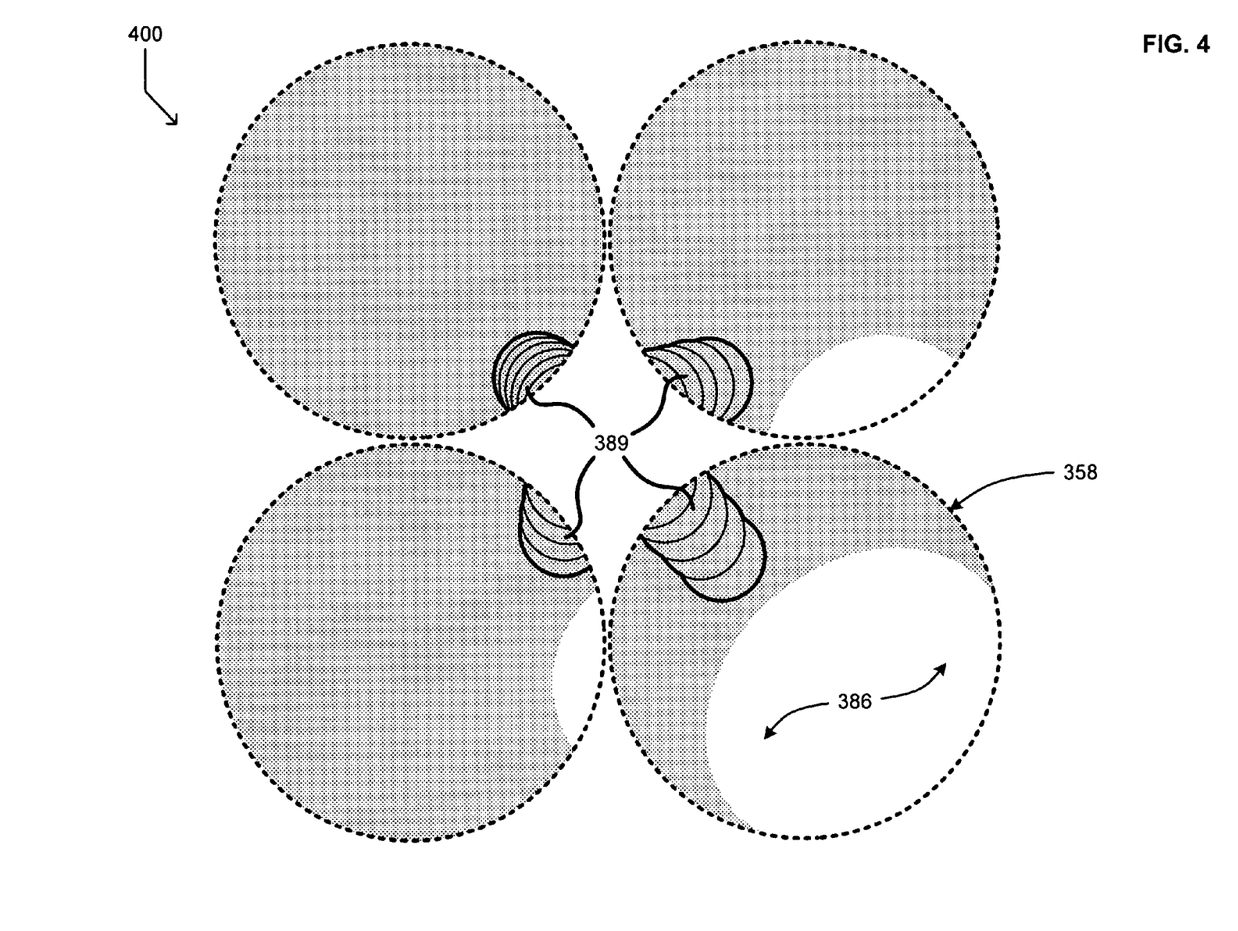
FIG. 4 depicts a type of image that can be generated by a system like that of FIG. 3.

Referring now to FIG. 4, there is shown an example of a type of image that can be generated by a system like that of FIG. 3. Imaging circuitry 333 of FIG. 3 can generate composite image 400, in some embodiments including a view 358 for each of the one or more lenses 316. Each of the several views shows that extension 389 bends toward the lens 316 nearest wall 386, against which balloon 313 is pressed. In the absence of blood, a portion of wall 386 is clearly viewable. Composite image 400 can provide a clearer view of extension 389 as it bends in any (lateral) direction.

Figure 5:
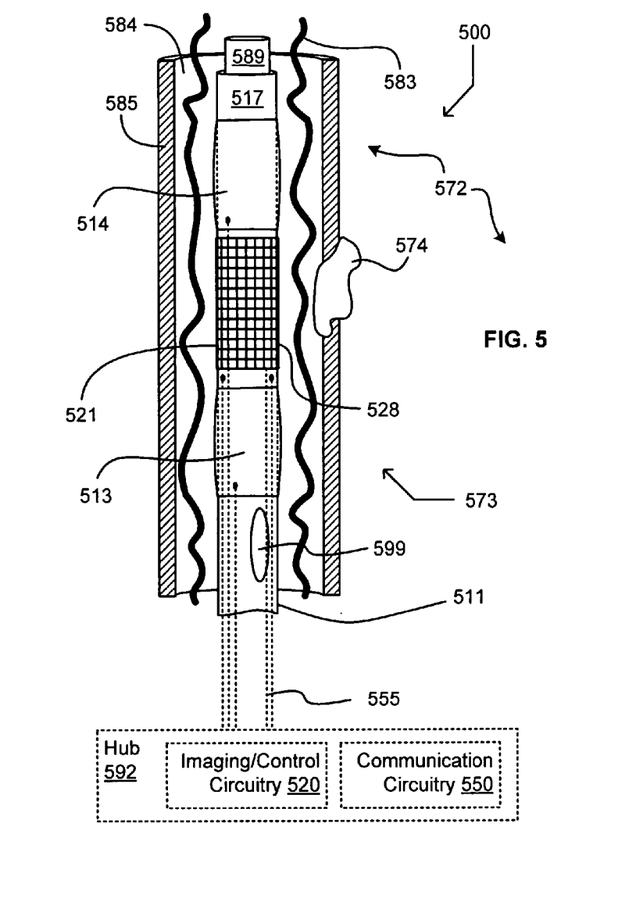
FIG. 5 depicts another exemplary environment in which one or more technologies may be implemented.

Referring now to FIG. 5, there is shown another exemplary environment in which one or more technologies may be implemented. As shown system 500 comprises vascular probe 511 having at least an intravascular portion 517 inside blood vessel 584 of a subject's vascular system. Intravascular portion 517 can include hub 592 comprising one or more of imaging/control circuitry 520 or communication circuitry 550. Blood vessel 584 is shown in a vicinity 573 of anomaly 574, with blood 583 flowing (downward) all around between intravascular portion 517 and wall 585 of blood vessel 584. Anomaly 574 protrudes somewhat radially from wall 585 into surrounding tissue 572. Imaging array 521 is arranged about the circumference of intravascular portion 517, including many elements 528 generally oriented radially.

With balloon 513 and other deflector 514 deflated, intravascular portion 517 can easily advance upward using extension 589 comprising a guidewire until, for example, imaging/control circuitry 520 can detect anomaly 574 (via element 528 and conduit 555, e.g.). Because of the presence of extension 589, also, port 599 is substantially closed to blood flow.

Figure 6:
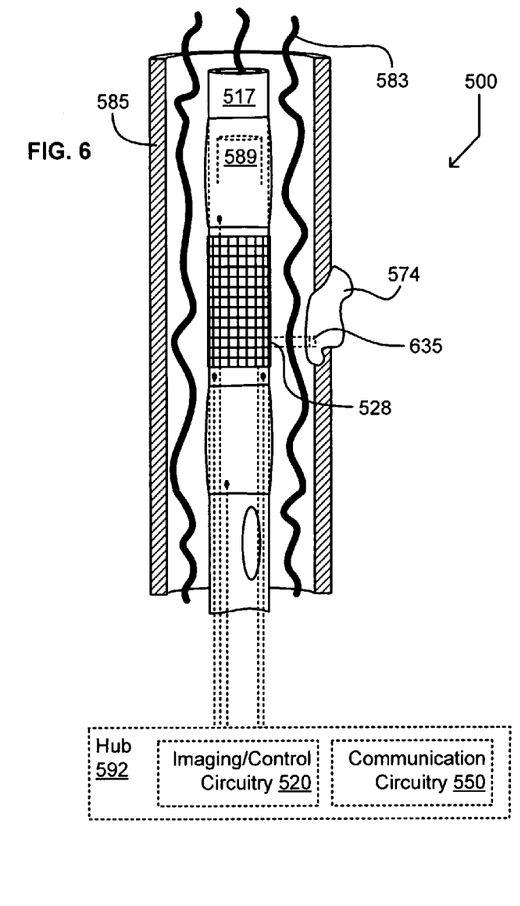
FIGS. 6-10 each depict the environment of FIG. 5 in a different circumstance.

Referring now to FIG. 6, there is shown system 500 of FIG. 5 in another circumstance. Element 528 has detected anomaly 574 within its field of view 635, and can stop for a better image, optionally automatically. Roughly at the same time, extension 589 can be at least partly withdrawn so that blood 583 can enter the large conduit from which extension 589 is being withdrawn.

Figure 7:
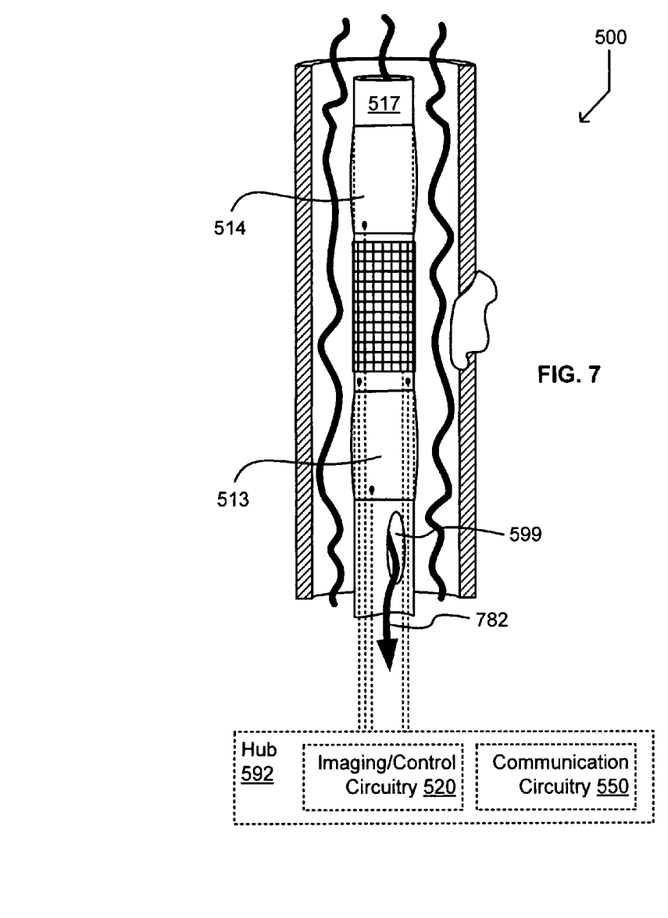

Referring now to FIG. 7, there is shown system 500 of FIG. 5 in yet another circumstance. Here, element 589 is withdrawn substantially without inflating balloon 513 or deflector 514. In this position, blood flow 782 is enhanced, relative to the position of FIG. 6, by flow 782 passing through port 599.

Figure 8:
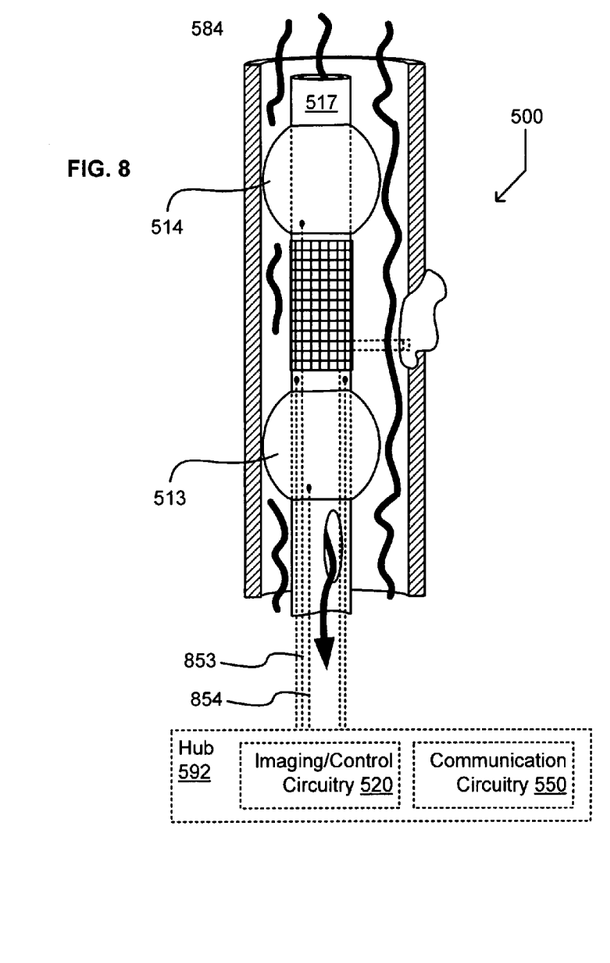

Referring now to FIG. 8, there is shown system 500 of FIG. 5 in yet another circumstance. Here, element 589 is still withdrawn, and balloon 513 and deflector 514 are partly inflated via line 853 and line 854, respectively.

Figure 9:
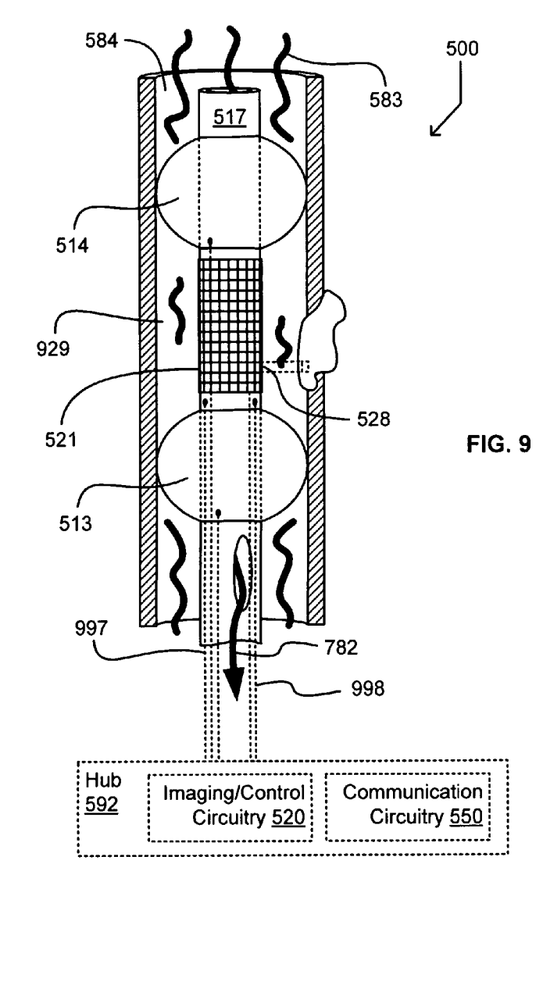

Referring now to FIG. 9, there is shown system 500 of FIG. 5 in yet another circumstance. Here, element 589 is still withdrawn, and balloon 513 and deflector 514 are substantially inflated. To remove a volume of the blood from volume 929 around imaging array 521, line 998 is used for suction (drawing blood out, e.g.). Optionally, line 997 is similarly used for injecting a fluid (saline or water, e.g.) to further clarify volume 929.

Figure 10:
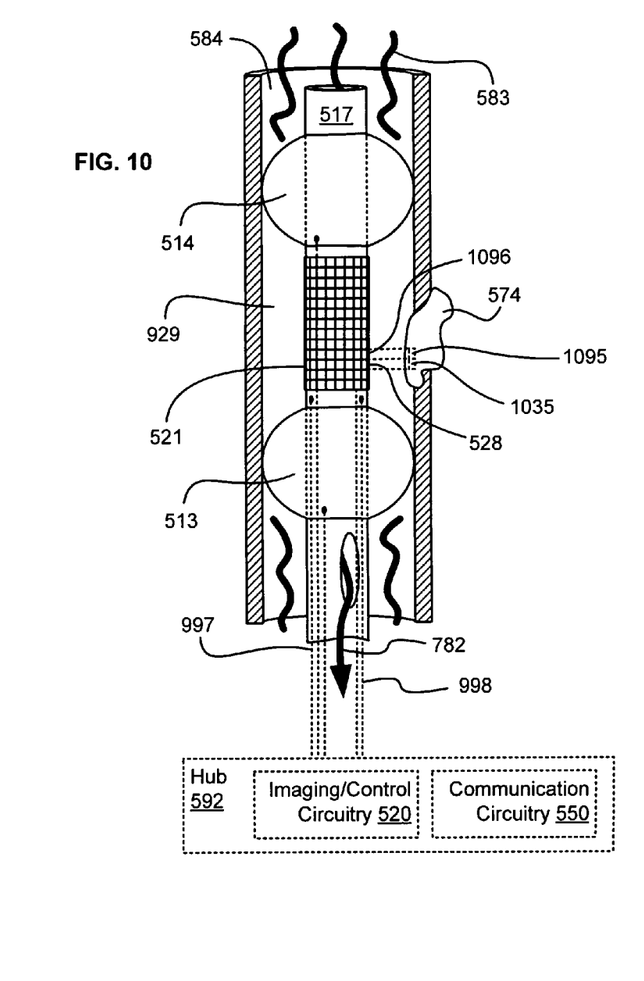

Referring now to FIG. 10, there is shown system 500 of FIG. 5 in yet another circumstance (e.g. a better circumstance for imaging in visible light, for example). Here, element 589 is still withdrawn so that flow 782 remains open. Balloon 513 and deflector 514 remain substantially inflated so that a tube-shaped interior of blood vessel 584 is not filled with blood. Substantially all of the blood from volume 929 around imaging array 521 has been replaced or otherwise removed, and imaging array 521 can capture a much better set of images at or above visible frequencies. In some embodiments, a light source such as emitter 1096 provides ablation, for example, to treatment field 1095, substantially adjacent field of view 1035.

Figure 11:
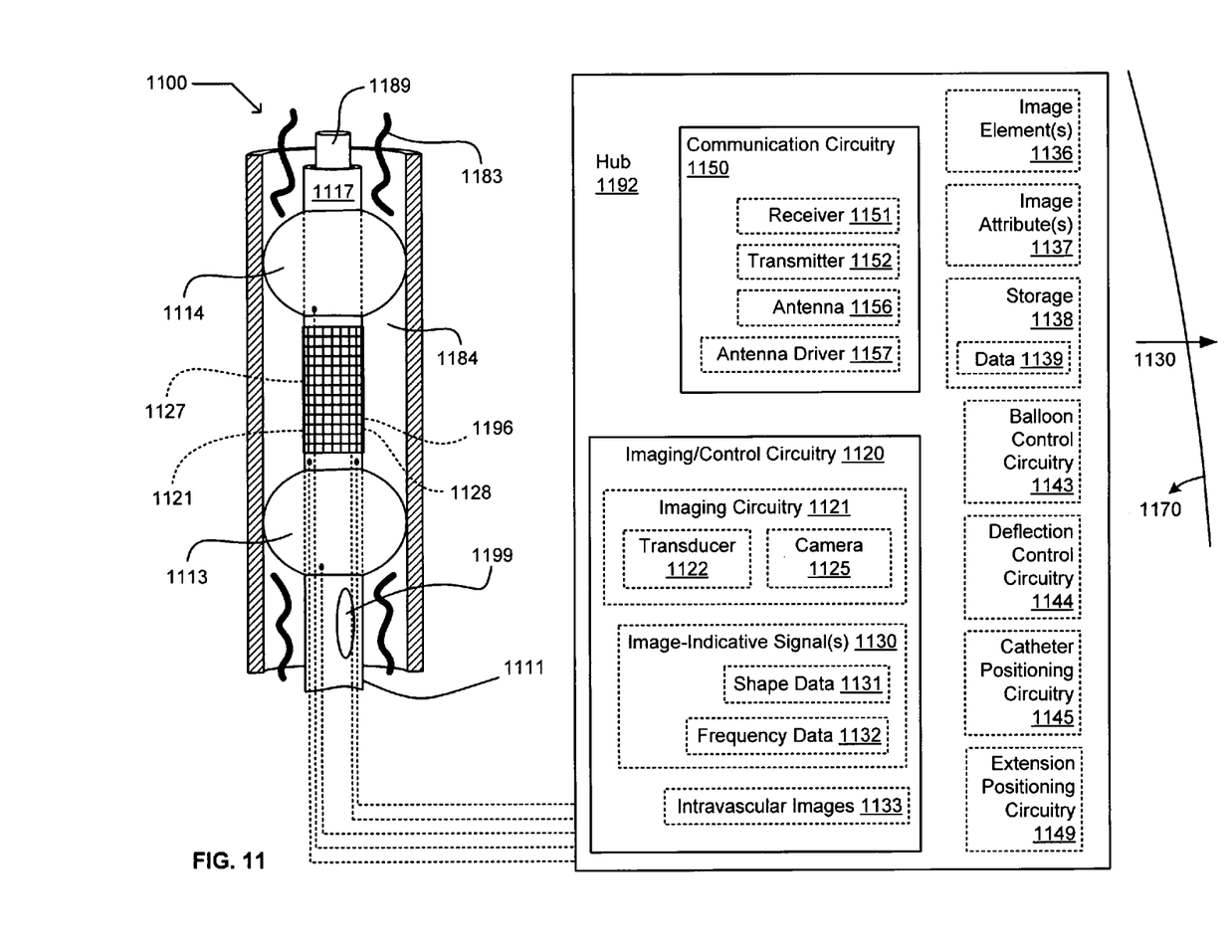
FIG. 11 depicts another exemplary environment in which one or more technologies may be implemented.

Referring now to FIG. 11, there is shown system 1100 that can essentially function as described above with reference to system 500 of FIGS. 5-10. Vascular probe 1111 comprises at least a distal intravascular portion 1117 inside artery 1184 of a subject's vascular system. Portion 1117 can include hub 1192 comprising one or more of imaging/control circuitry 1120 or communication circuitry 1150.

For example, extension 1189 can be at least partly withdrawn so that blood 1183 can enter the large conduit from which extension 1189 is withdrawn. Element 1189 can be withdrawn with or without inflating balloon 1113 or deflector 1114. Blood flow can be enhanced or preserved by blood flow passing through port 1199. In some embodiments, port 1199 comprises a tricuspid valve for substantially reducing oppositely-directed flow. Balloon 1113 can be inflated or deflated via lines 1183, and deflector 1114 can be inflated or deflated via line 1184. A volume of the blood around imaging circuitry 1121 can be drawn out via line 998, and a fluid can be injected into the same volume as line 997, optionally until substantially all of the blood from that volume has been removed or replaced. Imaging circuitry 1121 can then capture a clearer set of images. In some embodiments, a light source such as emitter 1196 provides ablation, for example, substantially adjacent a field of view of element 1128.

Imaging/control circuitry 1120 can include imaging circuitry 1121, optionally with one or more of light transducer(s) 1122, camera 1125, charge coupled device (CCD) array 1127, element 1128, and emitter 1196. Alternatively or additionally, imaging/control circuitry 1120 comprises image-indicative signals 1130 or intravascular images 1133. Image-indicative signals 1130 can optionally comprise one or more of shape data 1131 or frequency data 1132.

Communication circuitry 1150 can optionally comprise one or more of receiver 1151, transmitter 1152, antenna 1156, or antenna driver 1157 able to communicate the image-indicative signal 1130 outside the subject's body 1170.

Finally, hub 1192 can include one or more of image element(s) 1136, image attribute(s) 1137, storage 1138 containing data 1139, balloon control circuitry 1143, deflection control circuitry 1144, catheter positioning circuitry 1145, and extension positioning circuitry 1149.

Figure 12:
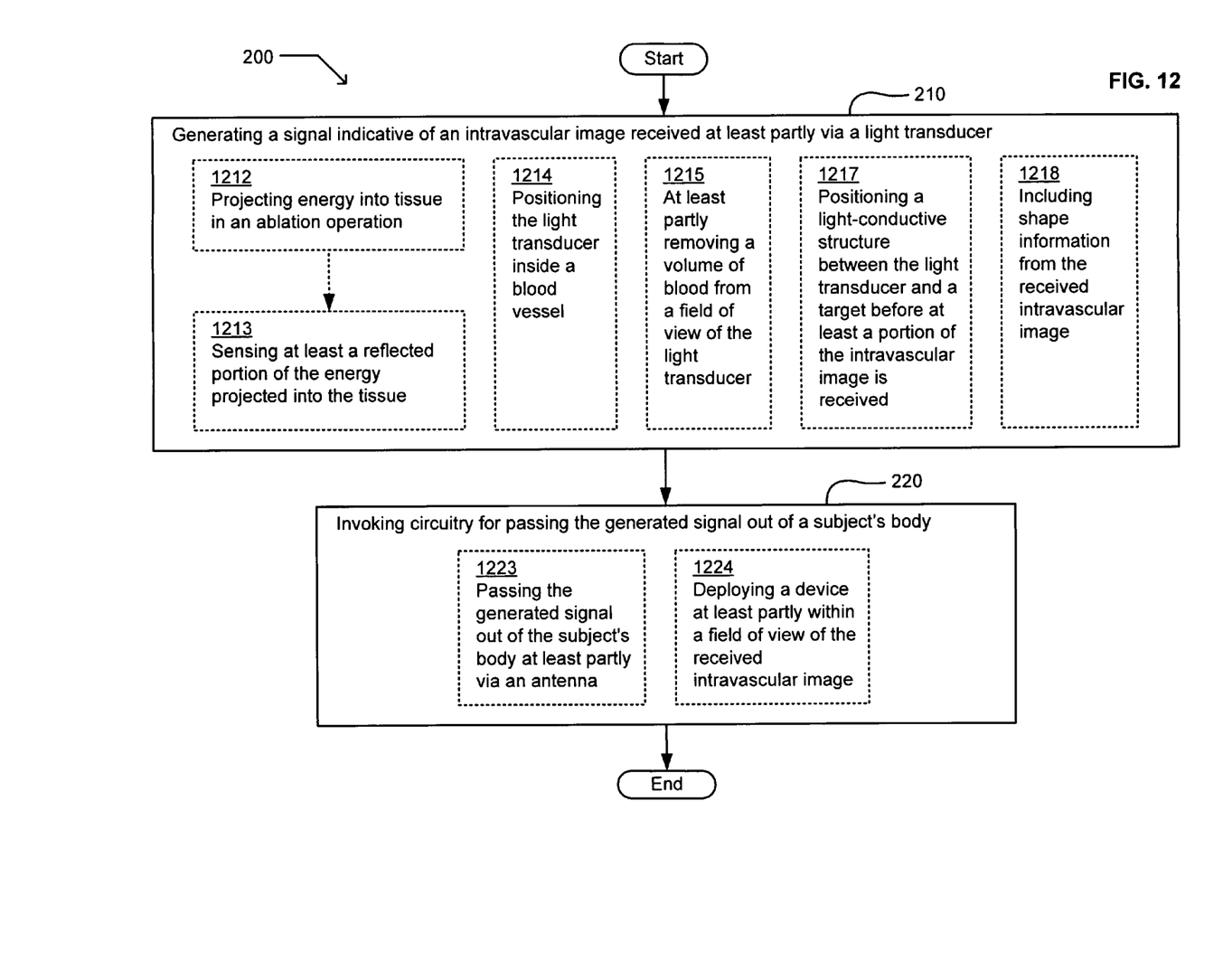
FIGS. 12-15 each depict several variants of the flow of FIG. 2.

Referring now to FIG. 12, there are shown several variants of the flow 200 of FIG. 2. Operation 210—generating a signal indicative of an intravascular image received at least partly via a light transducer—may include one or more of the following operations: 1212, 1213, 1214, 1215, 1217, or 1218. Operation 220—for passing the generated signal out of a subject's body—may include one or more of the following operations: 1223 or 1224.

Operation 1212 describes projecting energy into tissue in an ablation operation (e.g. emitter 1096 of FIG. 10 projecting a laser treatment to treatment field 1095 of anomaly 574). In some embodiments, the energy can be emitted from a source outside a subject's body, such as a portion of the external imaging system 168.

Operation 1213 describes sensing at least a reflected portion of the energy projected into the tissue (e.g. element 528 receiving a portion of the energy projected by emitter 1095 into anomaly 574). The reflected portion can be reflected once or more within anomaly 574, for example, if anomaly 574 a typically translucent biological material.

Operation 1214 describes positioning the light transducer inside a blood vessel (e.g. deflection control circuitry 344 or laterally moving imaging/control circuitry 320, including transducer 322). This can occur, for example, in embodiments in which at least imaging/control circuitry 320 performs operation 210 and in which at least communication circuitry 350 can be invoked in performing operation 220. In some embodiments, catheter positioning circuitry (not shown) can axially advance and retract intravenous portion 317 automatically by any of several techniques such as pushing, magnetic navigation, steering, or the like. See U.S. Pat. No. 6,610,007 issued to Belson et al., "Steerable Segmented Endoscope and Method of Insertion." See also U.S. patent application Ser. No. 11/062,074 by Leeflang et al., "Variable Steerable Catheters and Methods for Using Them." In other embodiments, the image is intravascular irrespective of the positioning of light transducer 322, by virtue of an imaging target being situated inside a blood vessel.

Operation 1215 describes at least partly removing a volume of blood from a field of view of the light transducer (e.g. hub 592 drawing a volume of blood 583 from volume 929 through line 998). In some embodiments, a replacement fluid such as saline or water is introduced roughly contemporaneously with the removing (e.g. via line 997).

Operation 1217 describes positioning a light-conductive structure between the light transducer and a target before at least a portion of the intravascular image is received (e.g. catheter positioning circuitry 345 positioning catheter 315, before image capture, so that one or more lenses 316 pass light between camera 325 and a field of view 335 around extension 389). The light-conductive structure can include an optical fiber or other solid or free space medium, for example, as an alternative to or in addition to the substantially transparent fluid exemplified in FIG. 10.

Operation 1218 describes including shape information from the received intravascular image (e.g. image receiving circuitry 321 recording a non-uniformity of intensity or hue among elements of CCD array 327 within video images 334 from camera 325).

Operation 1223 describes passing the generated signal out of the subject's body at least partly via an antenna (e.g. antenna driver 357 transmitting at least a binary indication of the above-referenced non-uniformity via antenna 356).

Operation 1224 describes deploying a device at least partly within a field of view of the received intravascular image (e.g. hub 392 unwinding spool 393 to drive extension 389 further in a distal direction). Extension 389 can include a conduit for injecting fluid or light into the body, for example, or for drawing out materials. Alternatively or additionally, extension 389 can comprise a needle, a Guglielmi Detachable Coil (GDC) wire, a clip, a valve, a guide wire, a stent, or the like.

Figure 13:
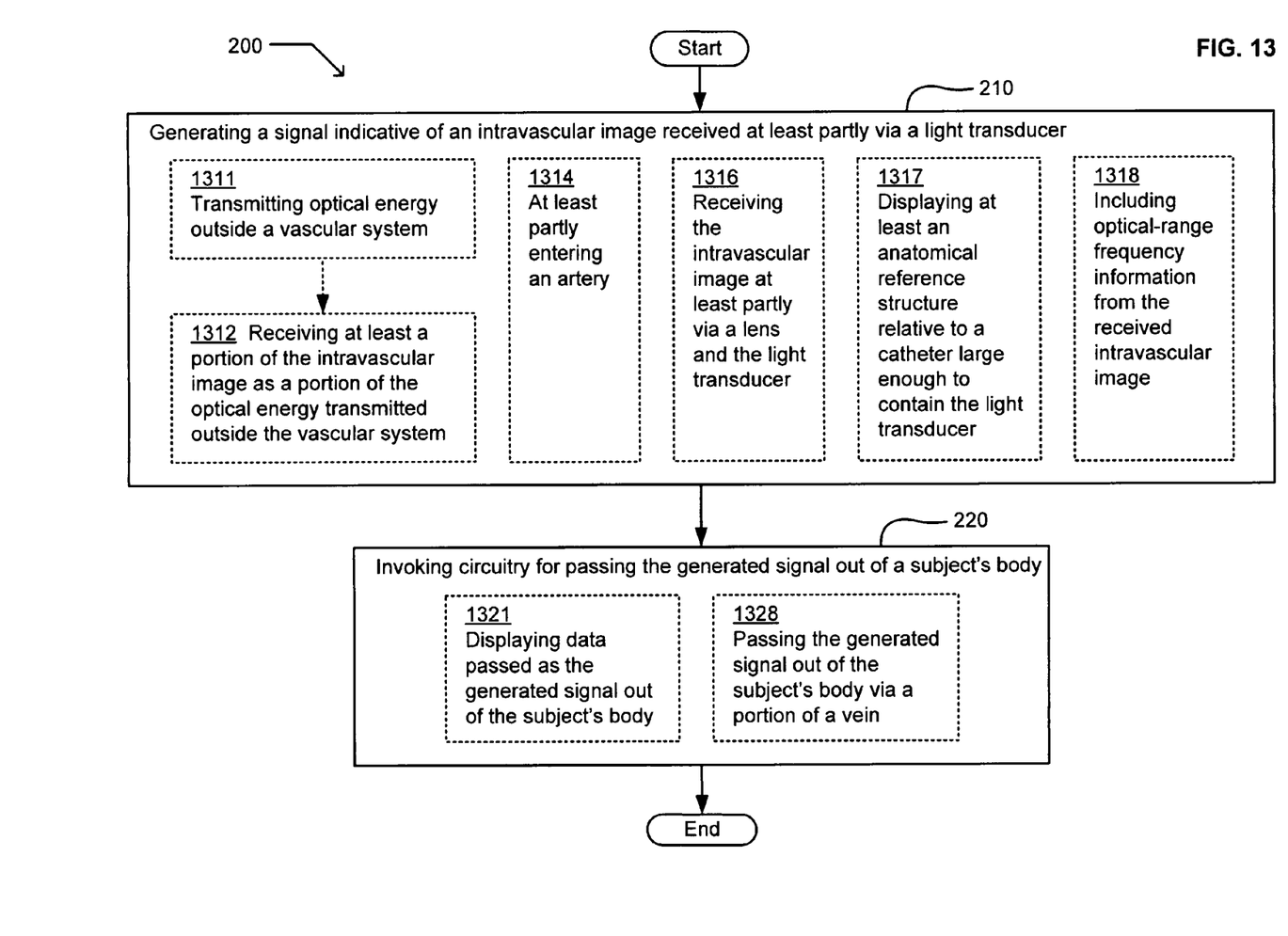

Referring now to FIG. 13, there are shown several variants of the flow 200 of FIG. 2 or 12. Operation 210—generating a signal indicative of an intravascular image received at least partly via a light transducer—may include one or more of the following operations: 1311, 1312, 1314, 1316, 1317 or 1318. Operation 220—for passing the generated signal out of a subject's body—may include one or more of the following operations: 1321 or 1328.

Operation 1311 describes transmitting optical energy outside a vascular system (e.g. external imaging system 168 emitting energy 104 into body 170). In some environments such as blood vessels near the skin, ambient fluorescent light or an external synchronized pulse like a camera flash can be used to provide the energy. For other environments, low frequency light (at or below that of near infrared, e.g.) and/or an internal source (emitter 1196, e.g.) of the energy can transmit the energy outside the vascular system (to tissue 172 or 572, e.g.).

Operation 1312 describes receiving at least a portion of the intravascular image as a portion of the optical energy transmitted outside the vascular system (e.g. optical inlet of light transducer 122 receiving a portion of emitted energy 104 not absorbed by tissue 172). Alternatively or additionally, camera 1125 or CCD array 1127 can receive a portion of the optical energy transmitted outside the vascular system via line 1153 and emitter 1196.

Operation 1314 describes at least partly entering an artery (e.g. vascular probe 1112 partly entering artery 1184). In some embodiments positioning and imaging circuitry described herein can be used in concert with one or more sampling or treatment operations performed via extension 1189 such as placing a stent or GDC wire, a biopsy, or the like.

Operation 1316 describes receiving the intravascular image at least partly via a lens and the light transducer (e.g. a memory or other imaging circuitry 333 receiving and stitching together respective images from lenses 316 via light transducer(s) 322). The stitching operation combines data from different fields of view into at least image data 339 that can be viewed in a common window of screen 362. See FIG. 4. These can occur, for example, in embodiments in which at least imaging/control circuitry 320 performs operation 210 and in which at least communication circuitry 350 can be invoked in performing operation 220.

Operation 1317 describes displaying at least an anatomical reference structure relative to a catheter large enough to contain the light transducer (e.g. display 162 and/or external imaging system 168 showing a probe portion 118 relative to structure 175). In some embodiments, an external image indicating a probe and an image obtained via the probe are shown in a common screen (screen 362, e.g.) or otherwise at least roughly simultaneously.

Operation 1318 describes including optical-range frequency information from the received intravascular image (e.g. image attribute(s) containing a number indicating a light frequency or wavelength describing the intravascular image).

In some embodiments, the frequency information comprises a prevalent wavelength or other description of a solid or other detected material. See U.S. Pat. No. 6,816,743 issued to Moreno et al., "Methods and Apparatus for In Vivo Identification and Characterization of Atherosclerotic Plaques."

Operation 1321 describes displaying data passed as the generated signal out of the subject's body (e.g. screen 362 displaying intravascular/video images 334 as one or more image-indicative signals 330). The one or more image-indicative signals can each include shape data 331, frequency data 332, an error signal such as a binary indication of a detected anomaly, or the like.

Operation 1328 describes passing the generated signal out of the subject's body via a portion of a vein (e.g. transmitter 352 transmitting an output of imaging circuitry 333 via a portion of conduit 355 within intravenous portion 317 of catheter 315). In some embodiments, substantially the entire intravascular signal path is intravenous.

Figure 14:
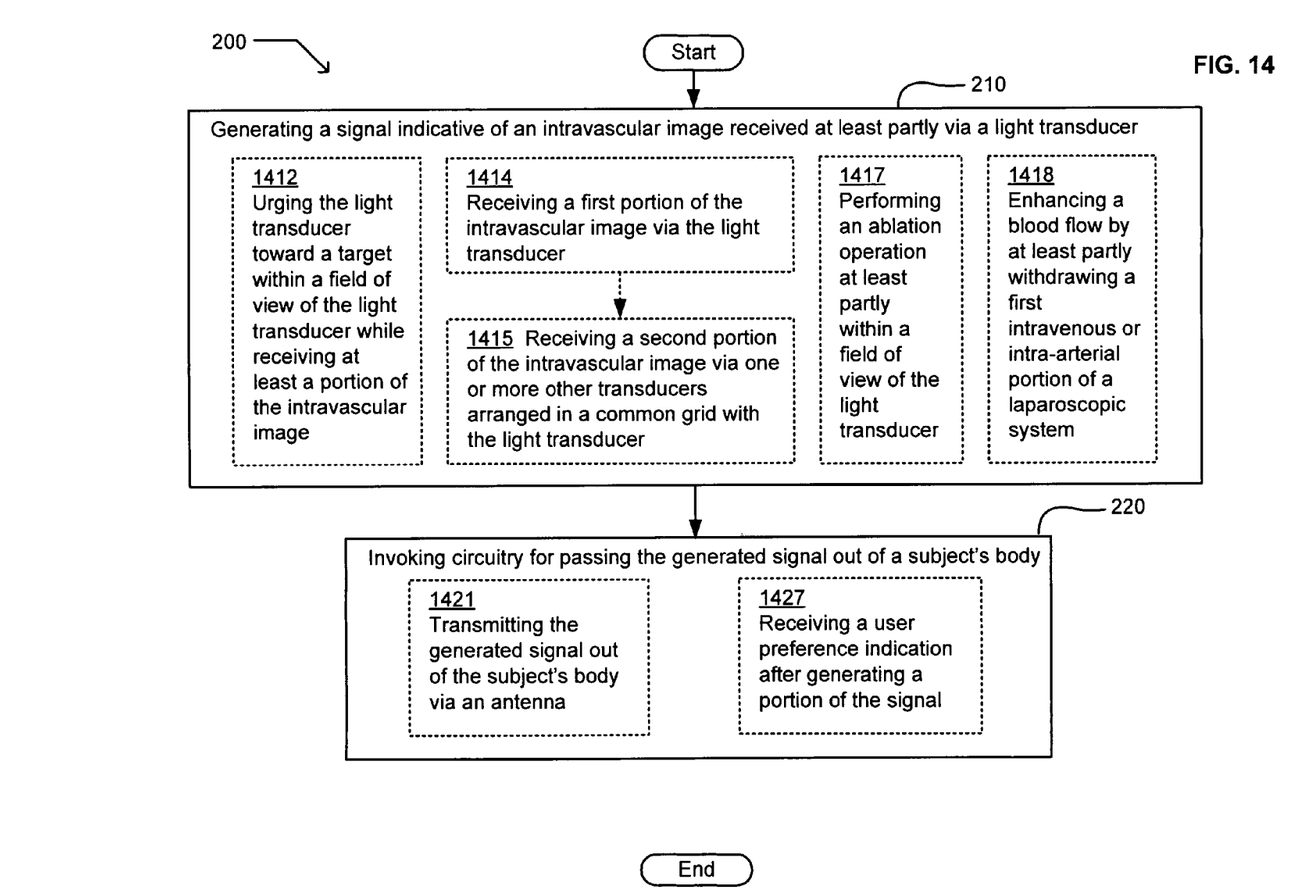

Referring now to FIG. 14, there are shown several variants of the flow 200 of FIG. 2, 12 or 13. Operation 210—generating a signal indicative of an intravascular image received at least partly via a light transducer—may include one or more of the following operations: 1412, 1414, 1415, 1417 or 1418. Operation 220—for passing the generated signal out of a subject's body—may include one or more of the following operations: 1421 or 1427.

Operation 1412 describes urging the light transducer toward a target within a field of view of the light transducer while receiving at least a portion of the intravascular image (e.g. deflection control circuitry and deflector 314 jointly urging one of the light transducer(s) 322 substantially toward wall 386 to which it is closest). In some embodiments, substantially all liquid blood between a light transducer and at least a target portion of its field of view can be removed before the image is received and captured.

Operation 1414 describes receiving a first portion of the intravascular image via the light transducer (e.g. at least imaging/control circuitry 1120 receiving a first of intravascular images 1133 at least partly via an element of CCD array 1127). This can occur, for example, in embodiments in which imaging/control circuitry 1120 and CCD array 1127 jointly perform operation 210, in which the received portions and images are stored as data 1139 of storage 1138 and in which at least communication circuitry 1150 performs operation 220. In some embodiments, operation 220 comprises physically removing storage 1138 from body 1170. In other embodiments, operation 220 comprises transmitting storage 1138 keeping a copy of image-indicative signals 1130 at least throughout operation 220, such as for archiving or possible later use.

Operation 1415 describes receiving a second portion of the intravascular image via one or more other transducers arranged in a common grid with the light transducer (e.g. at least imaging/control circuitry 1120 receiving a second of intravascular images 1133 at least partly via another element of CCD array 1127). This can occur, for example, in embodiments in which each of the intravascular images 1133 is a serially transmitted pixel having several bits of color information that are later stored as data 1139. In some embodiments, data 1139 includes the entire intravascular image indicated by the generated signal recited in operation 210. In some embodiments, data 1139 includes a multiple-pixel portion of a very large intravascular image and does not simultaneously include the entire image.

Operation 1417 describes performing an ablation operation at least partly within a field of view of the light transducer (e.g. at least extension control circuitry 345 and extension 389 projecting optical ablation energy within a field of view 335 of each of one or more lenses 316). This can occur, for example, in embodiments in which at least imaging/control circuitry 320 performs operation 210 and in which at least communication circuitry 350 can be invoked in performing operation 220.

Alternatively or additionally, in some embodiments extension control circuitry 345 can fully retract extension 389 (by winding spool 393, e.g.). It can then be replaced (by replacing spool 393, for example) by an extension having another function (GDC wire or stent installation or generating laparoscopic ultrasound images, e.g.).

Operation 1418 describes enhancing a blood flow by at least partly withdrawing a first intravenous or intra-arterial portion of a laparoscopic system (e.g. extension positioning circuitry 1149 withdrawing extension 1189 to open a flow path through port 1199). In some embodiments, operation 1418 can likewise be performed primarily by withdrawing a fluid as the first intravenous or intra-arterial portion (by drawing fluid out through line 853 or 854, deflating deflector 514 or balloon 513 respectively). The fluid may be a liquid, air or some other gas, a combination of more than one type of fluid, or the like.

Operation 1421 describes (e.g. communication circuitry 150 transmitting the generated signal via path 155 implemented as an antenna to receiver 164 and from transmitter 163). In some embodiments, for example, vascular probe 111 can be implemented for remote operation and configured for short range radio frequency communication.

Operation 1427 describes receiving a user preference indication after generating a portion of the signal (e.g. receiver 351 receiving a "capture image" signal via input device(s) 369 after detecting a presence of sufficient light for imaging in at least one of the fields of view 335). In some embodiments, operation 1227 is performed by an element partly inside a subject's body. In some embodiments, the user preference indication is received as a wireless signal.

Figure 15:
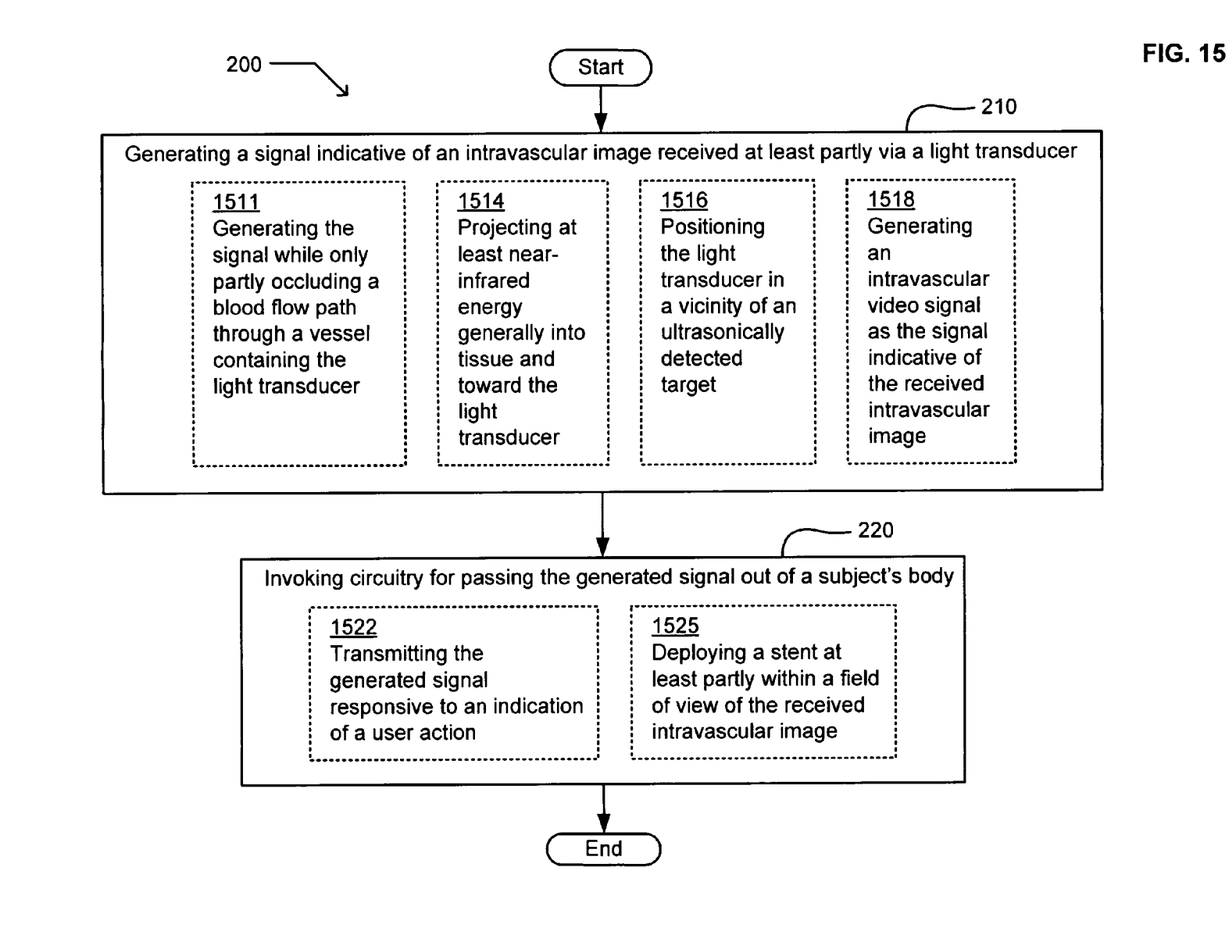

Referring now to FIG. 15, there are shown several variants of the flow 200 of FIG. 2, 12, 13, or 14. Operation 210—generating a signal indicative of an intravascular image received at least partly via a light transducer—may include one or more of the following operations: 1511, 1514, 1516 or 1518. Operation 220—for passing the generated signal out of a subject's body—may include one or more of the following operations: 1522 or 1525.

Operation 1511 describes generating the signal while only partly occluding a blood flow path through a vessel containing the light transducer (e.g. imaging circuitry 1121 and balloon control circuitry 1143 jointly generating a best available image with balloon 1113 inflated enough to stabilize portion 1117 while only partly blocking artery 1184). This can occur, for example, in embodiments in which at least imaging/control circuitry 1120 performs operation 210 and in which at least communication circuitry 1150 is invoked in performing operation 220. In some embodiments, element 1128 is configured for imaging with ultrasound or infrared radiation through blood. Further analysis can be performed by removing part or all of the blood from the field of view of CCD array 1127 and then by imaging with CCD array 1127.

Operation 1514 describes projecting at least near-infrared energy generally into tissue and toward the light transducer (e.g. at least external imaging system 168 emitting energy 104 generally rightward as shown, so that light transducer 122 can absorb a portion of the energy not absorbed or reflected back by tissue 172). In some embodiments emitted energy 104 also comprises a substantial component of infrared and lower-frequency light as well.

Operation 1516 describes positioning the light transducer in a vicinity of an ultrasonically detected target (e.g. deflection control circuitry 344 moving at least light transducer(s) 322 toward wall 386 responsive to detecting wall 386 ultrasonically). In some embodiments, for example, the ultrasonic detection can be performed extracorporeally or via extension 389 (implemented as an ultrasonic detector, e.g.).

Operation 1518 describes generating an intravascular video signal as the signal indicative of the received intravascular image (e.g. at least imaging circuitry 333 and image receiving circuitry 321 jointly generating an intra-coronary video signal). In some embodiments, a substantially live signal can thus be passed to screen 362 (in operation 220, e.g.).

Operation 1522 describes transmitting the generated signal responsive to an indication of a user action (e.g. communication circuitry and hub 392 displaying the above-described live video signal to screen responsive to an indication of a menu selection event). In some embodiments, the user action modifies a default or other configuration that has no effect upon the transmission until triggered by a later event (e.g. changing a default imaging mode to "video" responsive to a user action, even with no imaging data yet available).

Operation 1525 describes deploying a stent at least partly within a field of view of the received intravascular image (e.g. at least extension control circuitry 345 deploying a stent via extension 389 responsive to detecting a lesion in blood vessel 384 treatable by the stent).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Moreover, "can" and "optionally" and other permissive terms are used herein for describing optional features of various embodiments. These terms likewise describe selectable or configurable features generally, unless the context dictates otherwise.

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly.

What is claimed is:

1. An intravascularly positionable system comprising:
    circuitry configured for receiving one or more signals from at least one light transducer;
    circuitry configured for processing the one or more signals from at least one light transducer to generate data of at least one intravascular image; and
    circuitry configured for transmitting out of at least one subject's body the data of at least one intravascular image generated by processing the one or more signals from at least one light transducer.

2. The system of claim 1, wherein the circuitry configured for receiving one or more signals from at least one light transducer comprises:
    circuitry configured for receiving one or more signals from at least one light transducer associated with at least one lens.

3. The system of claim 1, wherein the circuitry configured for receiving one or more signals from at least one light transducer comprises:
    circuitry configured for receiving one or more signals from two or more light transducers.

4. The system of claim 1, wherein the circuitry configured for receiving one or more signals from at least one light transducer comprises:
    circuitry configured for receiving one or more signals from two or more light transducers having different fields of view.

5. The system of claim 1, wherein the circuitry configured for receiving one or more signals from at least one light transducer comprises:
    circuitry configured for receiving one or more signals from two or more light transducers arranged in one or more grids.

6. The system of claim 1, wherein the circuitry configured for receiving one or more signals from at least one light transducer comprises:
    circuitry configured for receiving one or more signals from at least one light transducer positioned within at least one inflatable element.

7. The system of claim 1, wherein the circuitry configured for receiving one or more signals from at least one light transducer comprises:
    circuitry configured for receiving one or more signals from at least one light transducer positioned beside at least one inflatable element.

8. The system of claim 1, wherein the circuitry configured for receiving one or more signals from at least one light transducer comprises:
    circuitry configured for receiving one or more signals from at least one light transducer positioned between two or more inflatable elements.

9. The system of claim 1, wherein the circuitry configured for processing the one or more signals from at least one light transducer to generate data of at least one intravascular image comprises:
    circuitry configured for processing the one or more signals from at least one light transducer to generate data of at least one intravascular video.

10. The system of claim 1, wherein the circuitry configured for processing the one or more signals from at least one light transducer to generate data of at least one intravascular image comprises:
    circuitry configured for processing the one or more signals from at least one light transducer to generate data of at least one intravascular composite image.

11. The system of claim 1, wherein the circuitry configured for transmitting out of at least one subject's body the data of at least one intravascular image generated by processing the one or more signals from at least one light transducer comprises:
    circuitry configured for transmitting out of at least one subject's body and upon at least one user action the data of at least one intravascular image generated by processing the one or more signals from at least one light transducer.

12. The system of claim 1, wherein the circuitry configured for transmitting out of at least one subject's body the data of at least one intravascular image generated by processing the one or more signals from at least one light transducer comprises:

circuitry configured for transmitting out of at least one subject's body via at least some vasculature the data of at least one intravascular image generated by processing the one or more signals from at least one light transducer.

13. The system of claim 1, wherein the circuitry configured for transmitting out of at least one subject's body the data of at least one intravascular image generated by processing the one or more signals from at least one light transducer comprises:
 circuitry configured for transmitting out of at least one subject's body via at least one antenna the data of at least one intravascular image generated by processing the one or more signals from at least one light transducer.

14. The system of claim 1, wherein the circuitry configured for transmitting out of at least one subject's body the data of at least one intravascular image generated by processing the one or more signals from at least one light transducer comprises:
 circuitry configured for storing the data of at least one intravascular image generated by processing the one or more signals from at least one light transducer.

15. The system of claim 1, further comprising:
 circuitry configured for signaling to project energy.

16. The system of claim 1, further comprising:
 circuitry configured for signaling to project energy in at least one ablation operation.

17. The system of claim 1, further comprising:
 circuitry configured for signaling to at least partially actuate at least one inflatable element.

18. The system of claim 1, further comprising:
 circuitry configured for signaling to at least partially occlude at least one blood flow path.

19. The system of claim 1, further comprising:
 circuitry configured for signaling to remove at least some blood.

20. The system of claim 1, further comprising:
 circuitry configured for signaling to at least partially actuate at least one channel.

21. The system of claim 1, further comprising:
 circuitry configured for signaling to release at least some fluid.

22. The system of claim 1, further comprising:
 circuitry configured for signaling to position at least one light transducer.

23. A method of operating an intravascularly positionable device comprising:
 receiving one or more signals from at least one light transducer;
 processing the one or more signals from at least one light transducer to generate data of at least one intravascular image; and
 transmitting out of at least one subject's body the data of at least one intravascular image generated by processing the one or more signals from at least one light transducer.

24. An intravascularly positionable device having one or more media bearing one or more instructions for facilitating operations comprising:
 receiving one or more signals from at least one light transducer;
 processing the one or more signals from at least one light transducer to generate data of at least one intravascular image; and
 transmitting out of at least one subject's body the data of at least one intravascular image generated by processing the one or more signals from at least one light transducer.

* * * * *